(12) United States Patent
Vouaux et al.

(10) Patent No.: US 12,357,475 B2
(45) Date of Patent: Jul. 15, 2025

(54) SIZER SYSTEM FOR ARTHROPLASTY

(71) Applicant: Aesculap AG, Tuttlingen (DE)

(72) Inventors: Alexis Vouaux, Poulangy (FR); Christophe Girouard, Sarcicourt (FR)

(73) Assignee: Aesculap AG, Tuttlingen (DE)

( * ) Notice: Subject to any disclaimer, the term of this patent is extended or adjusted under 35 U.S.C. 154(b) by 325 days.

(21) Appl. No.: 18/024,680

(22) PCT Filed: Sep. 2, 2021

(86) PCT No.: PCT/EP2021/074259
§ 371 (c)(1),
(2) Date: Mar. 3, 2023

(87) PCT Pub. No.: WO2022/053389
PCT Pub. Date: Mar. 17, 2022

(65) Prior Publication Data
US 2024/0024130 A1    Jan. 25, 2024

(30) Foreign Application Priority Data
Sep. 10, 2020 (EP) .................................. 20195454

(51) Int. Cl.
*A61F 2/46* (2006.01)
*A61B 17/17* (2006.01)
*A61F 2/38* (2006.01)

(52) U.S. Cl.
CPC ........ *A61F 2/4657* (2013.01); *A61B 17/1764* (2013.01); *A61F 2/3859* (2013.01);
(Continued)

(58) Field of Classification Search
CPC ............ A61F 2/4657; A61F 2002/4658; A61F 2002/4668; A61B 17/1764
See application file for complete search history.

(56) References Cited

U.S. PATENT DOCUMENTS

| 5,423,827 A | 6/1995 | Mumme et al. |
| 6,458,135 B1 | 10/2002 | Harwin et al. |

(Continued)

OTHER PUBLICATIONS

Extended Search Report received in European Application No. 20195454.2-1122 dated Mar. 29, 2021, with translation, 5 pages.
(Continued)

*Primary Examiner* — Samuel S Hanna
(74) *Attorney, Agent, or Firm* — Christopher A. Rothe; CM Law

(57) ABSTRACT

A femoral sizer system for knee arthroplasty includes a main block having a back surface that contacts a processed distal face of a femur. A fixed foot extends away from the back surface for posterior referencing. A docking unit docks with a connecting unit. An anterior stylus has a stylus tip for contact with an anterior face of the femur. The stylus is attachable to the main block and can adjust a position of the stylus tip. An orientation guide has referencing orientation points for implementing referencing pins in the femur. The orientation guide can be coupled to and uncoupled from the docking unit via its connecting unit with different sides of the orientation guide resulting in different positions of the orientation points relative to the main block, so that the femoral sizer system can be used for the right knee joint or the left knee joint.

19 Claims, 4 Drawing Sheets

(52) U.S. Cl.
CPC ............ *A61F 2002/4658* (2013.01); *A61F 2002/4668* (2013.01)

(56) References Cited

U.S. PATENT DOCUMENTS

| | | |
|---|---|---|
| 2004/0220583 A1 | 11/2004 | Pieczynski et al. |
| 2014/0148809 A1 | 5/2014 | Schmalzried et al. |
| 2015/0173774 A1* | 6/2015 | Leslie .............. A61F 2/4657 606/102 |

OTHER PUBLICATIONS

Search Report received in International Application No. PCT/EP2021/074259 dated Oct. 29, 2021, with translation, 3 pages.
Written Opinion received in International Application No. PCT/EP2021/074259 dated Oct. 29, 2021, with translation, 6 pages.

\* cited by examiner

SIZER SYSTEM FOR ARTHROPLASTY

CROSS-REFERENCE TO RELATED APPLICATIONS

This application is the United States national stage entry of International Application No. PCT/EP2021/074259, filed Sep. 2, 2021, and claims priority to European Application No. 20 195 454.2, filed Sep. 10, 2020. The contents of International Application No. PCT/EP2021/074259 and European Application No. 20 195 454.2 are incorporated by reference herein in their entireties.

FIELD

The present invention relates to a sizer system respectively to a sizer for joint arthroplasty, especially to a femoral sizer system for knee arthroplasty. Besides, the present invention relates to a knee arthroplasty system.

BACKGROUND

A joint or articulation is a connection between bones in a human body. Its special design allows different degrees and types of movement. Besides elbow- and shoulder joints there are knee-joints that are self lubricating and almost frictionless and are able to withstand heavy compressions and loads.

The knee joint enables a person's leg to flex and articulate during movement and connects the upper bone (femur as the proximal bone—relatively seen) to the lower bone (tibia as the distal bone). However, the knee joint may be rendered nearly or totally inoperative by extended and heavy use, disease, or trauma. Often, the best therapy is a total replacement (arthroplasty). During a total knee arthroplasty, the femoral and tibial surfaces that are joined at the knee are replaced with mechanical implant components.

Usually, after a preoperative planning, a distal femoral resection and a tibial proximal resection is executed and afterwards an anterior cut, a posterior cut and inserting of chamfers are carried out. Once the distal end of the femur has been processed, the size and orientation of a femoral component will be determined, especially by a position of the anterior and posterior condylar. A medial posterior condylar cut allows a prosthetic condylar surface to be at roughly the same level as in the non-arthritic knee.

If external rotation is desired, the external rotation can be set using special surgical techniques. In the normal knee there is laxity in the lateral compartment after approximately 20 degrees flexion, that allows the medial pivot action seen in normal knees. However, externally rotating the femoral component while possibly helping with patellar tracking makes the lateral posterior condyle more prominent than normal and may impede the medial pivot tracking motion seen in a normal knee. A reasonable compromise is to place an implant component at about an angle $\alpha=3$ degrees of external rotation for the left knee and for the right knee, with different signs for the respective knee.

Here, it needs an attempt to align the femoral sizer and later the femoral implant component with the Whiteside's line. When the sizer is correctly aligned, pins are placed or drilled through appropriate drilling holes in the sizer perpendicular to a cut surface of the distal femur (condyles). Hereafter, the sizer will be removed and a cutting block will be placed over the pins and a surgeon will finally determine, whether the position of the cutting block will result in cuts in the appropriate positions.

It is known from the prior art to provide a femoral sizer respectively a femoral sizer system that is capable of measuring the size of the femur. Herein one modular femoral sizer (system) of the prior art has a main block with a plate shaped base as feet for the sizer that is perpendicular to a back surface of the main block. A rotational orientation guide out of a set of a plurality of rotational orientation guides with different angles for external femoral rotation and according to the respective side (left, right) needs to be selected. The selected rotational orientation guide is connected to the main block as the posterior referencing femoral sizer by sliding them onto a plurality of pins in one specific direction. The posterior referencing femoral sizer is then placed flat against the cutting edge of the distal femur with both the posterior condyles secured to its base.

The main block further comprises a swivelling anterior stylus adaptable in its height and position. The height is lowered until the anterior stylus is brought into contact with the anterior surface ridge of the (lateral) anterior femoral cortex and the posterior main block and base are in contact with the medial and lateral posterior condyles. The size of the femur can then be seen on the front of the femoral sizer and a position of the sizer can be refined by selecting a size of the femur on the anterior stylus that is adjustable in its length.

The external rotation can also be checked taking into account the alignment to the so called epicondylar axis using a epicondylar axis reference. Once the position of the sizer is satisfactory, pre-drill and inserts of the pins through drilling holes can be performed.

However, the system is very complex due to the high number of different guides, and difficult to clean and to sterilize. The femoral sizer needs different orientation guides for the left knee as well as for the right knees. Further, the femoral sizer needs different orientation guides for different angles $\alpha$ of external rotation. Further, such a system demands a lot of time to find the right guide, especially for the left and right knee and will delay an operation and reduce an efficiency. In addition, the main block covers the sight onto the distal end of femur thus making it more difficult to recognize the transepicondylar axis as well as the Whiteside's line. Therefore, it is hard for a surgeon to correctly align the femoral sizer.

Another femoral sizer system according to the prior art uses a section with a receiving hole on a left and right side (when seen at the front) in order to assemble an anterior stylus on a left or right side of the knee (femur). This section is coupled via a swivel/rotating joint for rotating about an proximal-distal axis to two feet, in order to set an external rotation. A verification is made by lining up the epicondyles with reference lines marked on the section and another check is made to assess the Whiteside's line. Then the assembly is positioned on the resected distal femur, sliding the feet of the femoral sizer under the posterior condyles and the anterior stylus point rests on the anterior surface of the bone. A size is determined by a position of the scribe mark on the femoral anterior stylus shaft within the sizing.

However, such a femoral sizer system is hard to sterilize and is complicated to adjust since especially a view for a surgeon is severely limited. Further, once an external rotation is set, the system needs to be hold in place and is susceptible for errors.

Another femoral sizer system for measured femoral sizing and rotation comprises a rotation joint/swivelling joint and a size locking knob for fixing a femoral size and a pivoting anterior stylus. In this system, the sizer is placed against the resected surface of the distal femur with the posterior feet contacting the posterior condyles. A degree of external rotation is adjusted to be parallel to the epicondylar axis by squeezing a rotation lever and rotating an anterior section relative to the feet of the sizer. Rotation markings indicate the degree of external rotation. Then, a posterior-anterior position of the anterior stylus is adjusted to indicate the femoral component size. A line through anterior down pin holes indicates the size and the size position is locked by twisting a size locking knob. Universal pins are inserted through the pin holes/drilling holes for referencing.

However, the femoral sizer again is complicated to set on the femur and to remove from the femur. Further, the system is not easy to use without any prior introduction to the system and profound knowledge and the view of the surgeon is obstructed by mechanical adjustment components. In addition, there is a security risk regarding the loosening of the know and a loss of the measured size. And finally, it is difficult to assemble and to disassemble the system and to sterilize it.

SUMMARY

Therefore, it is an object of the invention to avoid or at least reduce the disadvantages of the prior art and in particular to provide a sizer system, especially a femoral sizer system, that allows to evaluate a size of a bone, especially of the femur that is simple in its structure and function and can be easily used without extensive know-how of adjustments of the system and that further minimizes an invasive intervention due to its design. Especially, the sizer/sizer system is small in construction space and reduces material used for its building. Further an improved visualization for an alignment (of the sizer system) to the anatomical landmarks as the Whiteside's line and the (trans-)epicondylar axis shall be provided, for a more precise and efficient intervention.

In short, the invention provides a modular sizer system, especially a modular femoral sizer system having a main block with an anterior stylus as well as a detachable (removable) reversible orientation guide/block that can be coupled and uncoupled to the main block. Due to its reversible design, this orientation guide can be used for a left joint as well as for a right joint, especially the left and right knee. The sizer system is adapted to use for one external rotation of a specific angle/degree, for example 3 degrees, only one (single) orientation guide for the left knee as well as for the right knee. The reversible orientation guide is configured to be attached to the main block with/in a first position and alignment relative to the main block as well as with/in a second position and alignment that is different to the first one, depending on its direction of attachment. The two referencing orientation points, preferably the two drilling holes, are, depending on the alignment, different and therefore two different angles of external rotation for the left and right knee can be implemented with just one reversible orientation guide. Thus, an amount of modular components can be reduced and the complexity of the system can be lowered, enabling the medical personal to more easily use the present sizer system. In addition, as described later on, such a design improves a visibility for a surgeon improving an intervention.

In other words, the (femoral) sizer system for (knee) arthroplasty comprises three main functional elements: a main block, an anterior stylus and a reversible orientation guide. The sizer system according to the present invention comprises the main block having a plane (femoral) back surface for being placed in contact with processed (femoral) condyles of a femur (distal face), at least one, preferably two, fixed feet (feet that are fixed/non adjustable, especially no rotatable) extending mainly perpendicular to and away from the plane (femoral) back surface for posterior referencing (posterior face of the femur), and a docking unit/section for docking/connecting with a corresponding connecting unit. The sizer system further comprises the anterior (surface) stylus having a stylus tip/point (free end of anterior stylus for referencing) for being placed in contact with an anterior face/anterior cortex of the femur, the anterior stylus being attached or attachable to the main block and being adapted to adjust a position of the stylus point. The sizer system further comprises the reversible orientation guide/block for external orientation having at least two referencing orientation points, especially in the form of two drilling holes, that are provided and adapted for implementing referencing pins in the femur and a connecting unit corresponding to and interacting with the docking unit, the reversible orientation guide being adapted to be reversibly, detachably coupled to and uncoupled from the docking unit of the main block (via the connecting unit) with two different sides of the reversible orientation guide facing the main block, so that the femoral sizer system is configured to be used for the right knee joint as well as for the left knee joint.

The directions used herein refer to the medical specifications of the human body and especially the femur, since the femur constitutes the main field of application. Herein, anterior and posterior reference a front side (anterior) and a back side (posterior) of the body or the femur. Further, medial and lateral reference an inner side (medial) and outer side (lateral) of the body and the femur. Proximal and distal reference to the main body (proximal) and from the main body away (distal). Of course, these directions can be put in relation or replaced by other directions such as X-Y-Z directions or the like. For example, the proximal-distal direction can be put in relation or replaced by the X-direction, the medial-lateral direction by the Y-direction and the anterior-posterior direction with the Z-direction in order to describe the present femoral sizer system without any reference to a human body. However, in the following the medical references for the femur are used since they are illustrative and easy to understand. It shall be noted that in the following the term "front side" of a component (not of the body) is used when viewed in the proximal direction, since usually the surgeon is looking in the proximal direction, especially for referencing. On the contrary, the term "back side" of a component, such as the back surface of the main block, is used when viewed in the distal direction.

The plane (femoral) back surface of the main block is aligned mainly parallel to a posterior-anterior direction (standing in contact with the distal face of the femur) and in the medial-lateral direction. In other words, the plane back surface extends in the anterior-posterior direction and in the medial-lateral direction. The at least one foot for posterior referencing, preferably the two feet, are extending perpendicular to the back surface (in the proximal direction) and in consequence are aligned mainly parallel in a proximal-distal direction (standing in contact with the posterior face of the femur). Preferably the at least one foot has a plane upper referencing surface that extends in the proximal-distal direction as well as in the medial-lateral direction (the referencing surface is parallel to them). Thus, this part of the main block, especially its referencing surfaces (plane back surface and referencing surface of the at least one foot), that is turned toward the femur, when viewed in the medial-lateral direction, is designed in a L-shape (with mainly or exact 90° between the two surfaces). With this shape of the main block, the degree of freedom of the main block is limited in two directions or in other and the present sizer system can be placed, aligned and later fixed easily to the processed distal end of the bone.

According to the invention, the reversible orientation guide has at least two referencing orientation points, preferably in the form of drilling holes, that are provided and adapted for implementing referencing pins in the femur for referencing anatomical landmarks. These referencing orientation points constitute the angle α of external rotation relative to the main block. Further, these two referencing orientation points and thereby the referencing pins are preferably, when the sizer system is correctly aligned to the Whiteside's line and to the transepicondylar axis, symmetrical aligned to the Whiteside' line and parallel to the transepicondylar axis. Thereby, the pins constitute the reference for a component, especially for a cutting block later on. The reversible orientation guide has the connecting unit corresponding to and interacting with the docking unit, the reversible orientation guide being adapted to be reversibly, detachably coupled to and uncoupled from the docking unit of the main block with at least two different sides of the reversible orientation guide, so that the femoral sizer system is configured to be used for the right knee joint as well as for the left knee joint. Preferably, the orientation guide has two outer sides/outer faces that are turned away/averted from each other or are roughly speaking on opposite sides of the orientation guide, that can be reversed or flipped and, depending on the orientation/alignment/direction of the orientation guide after reversing or flipping (by 180 degree), can be attached to the main block with the first outer side or the second outer side facing the main block. Thereby the orientation guide implements by the two referencing orientation points an angle α of external rotation relative to the main block having a positive degree or when flipped by 180 degree having the same angle of external rotation a but with a different sign, namely a negative sign. Thereby the reversible orientation guide is capable of being used for the left knee as well as for the right knee by just reversing/flipping the orientation guide. When the referencing orientation points are in the form of drilling holes that preferably extends in (parallel to) the proximal-distal direction, a surgeon can easily (pre-)drill the holes for the referencing pins and can afterwards continue his intervention.

With other words, the reversible orientation guide is configured to be assembled to be adjusted for an external rotation on the right knee joint as well as for the left knee joint. This only depends on a docking direction of the reversible orientation guide. Namely, the reversible orientation guide is provided and adapted to have/implement at least two docking directions for docking to the main block. In the first docking direction, the orientation guide implements a first angle of external rotation by its two referencing orientation points that are rotated by this angle of rotation about an axis in the proximal-distal direction (relative to the main block). In the second docking direction, the (same) orientation guide implements a second angle of external rotation by its two referencing orientation points that are rotated by the angle of rotation about an axis in the proximal-distal direction that is different to the first one. Especially the first angle of rotation is the same as second angle of external rotation but with a different sign (positive-negative, for example +3° and −3°).

By this, the sizer system is easy in use, robust having a reduced complexity. Further, due to its simple structure and its special boundary conditions, the femoral sizer system can be designed with a high degree of freedom, enabling the use of cut-outs, only little building material necessary and consequently a great improvement for a visualisation of an alignment of the sizer system, especially of the removable and reversible orientation guide/block to the anatomical landmarks such as the Whiteside's line and the transepicondylar axis alignment. The at least two referencing orientation points, preferably the two drilling holes, of the reversible orientation block serves as a reference for the next step of the surgery, such as a resection of the posterior side, adding chamfers and an anterior resection.

It is pointed out that the main block and/or the anterior stylus or the main block and/or the reversible orientation guide disclosed in the present invention can also be claimed independently in a separate application. These modules are delimited separate subject-matters itself. With other words, the main block itself or the anterior stylus itself or the reversible orientation guide itself can be claimed independently in a separate application as well as the combination of the main block and the anterior stylus or the combination of the main block and the reversible orientation guide.

In a preferred embodiment, the docking unit and the connecting unit are adapted to be form fitting together. In other words, the docking unit and the connecting unit are form fitting together via its geometry for a first side of the orientation guide facing the main block as well as for a second side, especially the side avers/averted/turned away from the first side, of the orientation guide facing the main block. The docking unit and the connecting unit are geometrically adapted to each other such that the docking unit fits to or in the connecting unit or vice versa. Preferably the docking section is in the form of a block protruding perpendicular to the femoral back surface in a direction opposite to the extension of the at least one feet (extending in the distal direction) and the reversible orientation guide comprises an corresponding guide opening/guide aperture complementary to the block as the connecting unit. With this configuration, the guide opening of the reversible orientation guide can be used for both averse sides of the reversible orientation guide. Alternatively, the configuration may be inversed such that the main block may have a main block opening and the reversible orientation guide may have a corresponding protruding block extending on both sides in the proximal-distal direction, in other words two protruding blocks on each side.

According to another preferred embodiment, the docking unit of the main block may be in the form of a block, preferably in the form of a rectangular block when viewed in the proximal direction, protruding perpendicular to the plane back surface in a direction opposite to the extension of the at least one feet. Thus, the block is protruding in the distal direction and the reversible orientation guide comprises a guide opening as the connecting portion that is complementary to the block to form a lock and key principle. When the docking unit is in form of the block that has preferably flat/plane side walls, the contour of its cross section is the same in the distal direction. Likewise, the guide opening of the orientation guide that serves as kind of an adapter to the block as the docking unit that has the same contour of its cross section, especially the same contour of the cross-section as the one of the block of the docking unit, fits onto the docking unit with both sides of the guide opening that goes throughout the entire orientation guide. In other words, since the continuously guide opening has two entrances for the docking unit on both sides of the orientation guide, the reversible orientation guide can be attached to the docking unit and thereby to the main block with two different sides of the orientation guide facing the main block.

Preferably, the length of the docking unit in the distal direction is the length of the guide opening in the distal direction. Preferably, the contour of the cross section of the docking unit in the proximal direction is slightly smaller the contour of the cross section of the connecting unit in the proximal direction, so that the orientation guide easily fits onto it. Preferably, the block of the docking unit has at least one, especially two chamfered edges in the distal direction. Preferably, the block has two of its edges that extend in the distal direction chamfered, wherein these two edges are the edges on its anterior side. The guide opening may be throughout the whole orientation guide or on both opposite sides of the orientation guide may be an guide opening, preferably aligned coaxially to each other.

Preferably, the docking unit of the main block may comprise, especially a spring biased, locking member, preferably in the form of a locking ball, that interacts with the connecting unit, preferably with a trough/tray of the connecting unit, in order to implement a snap-fit system to keep the reversibly orientation guide in place and to give a feedback to a user that the reversible orientation guide is connected properly. Specifically the docking unit in form of the block has a recess in its anterior surface, in which a locking ball and a spring member is inserted. The spring member, such as a spring or an elastic material such as rubber, pushes the locking ball in the anterior direction but due to geometric restrictions the locking ball cannot escape the block of the docking unit. In this way, the locking ball is spring biased in the anterior direction and forms, together with a recess or trough, especially a circular recess in the anterior surface of the guide opening, a snap-fit system.

According to another embodiment, the reversible orientation guide may be designed axial symmetrically except for the connecting unit that is rotated by an angle of rotation about an axis that is parallel to the respective symmetry plane. When viewed at a front, that is in the proximal direction in an assembled state, the orientation guide has relative to its axis of symmetry a left side and a right side that are the same structure and form and are mirrored on the axis of symmetry. However, the connecting unit is not symmetric or symmetrically aligned but rotated by an angle of external rotation about an axis in the proximal-distal direction (when in the assembled state). Thereby, since the connecting unit is the only part of the orientation guide that is connected to the main block, the whole orientation guide is rotated by this angle of external rotation as well, so that in an assembled state, the symmetric orientation block is rotated about exactly the angle of external rotation to the main block. Since the orientation guide is reversible attachable to the main block, with one side of the orientation guide the angel of external rotation is positive and with the other side, the angle of rotation is negative. Thereby, a orientation guide is provided that is capable of being used for a right knee as well as for a left knee since the orientations are different in signs.

According to another aspect of the invention, the reversible orientation guide may be, when viewed at a front side, in a T-shape, having two wing (shaped) portions (as the short parts of the T), especially in the form of a rain drop with an outwardfacing point, wherein each wing portion may comprise one of the at least two referencing orientation points, preferably in the form of the drilling holes, that are in a proximal-distal direction in an assembled state, for transepicondular axis alignment. In addition, the orientation guide may have an indicator wall that extends perpendicular to a virtual line connecting the two referencing orientation points, preferably in the form of the two drilling holes for referencing the Whiteside's line. The indicator wall is preferably flat and thin and has a smaller dimension in the medial-lateral direction (in an assembled state) than in the proximal-distal direction and/or the anterior-posterior direction. Preferably the indicator wall has an wall aperture in the medial-lateral direction in order to minimize a weight and to optimize a visual view for a surgeon. Preferably, the indicator wall is in the form of a plane metal sheet that has when viewed in the lateral-medial direction, a rectangular outer contour with an rectangular inner contour of the wall aperture. Preferably the outer surfaces of the indicator wall that faces/point to the anterior direction, the proximal direction and the distal direction are chamfered, preferably on all edges of its respective sides in the proximal, anterior and distal direction. This helps to improve a visual view for a surgeon.

Preferably, except for the connecting unit, the reversible orientation guide is axis symmetric to a first symmetry plane as well as to a second symmetry plane that stands perpendicular to the first symmetry plane. Especially the first symmetry plane extends in the proximal-distal direction and the second symmetry plane extends in the medial-lateral direction. Thus, except for the connecting unit that specifies an angle of external rotation, the orientation guide has the same "front side" as the first side and "back side" as the second side as well as the "same left" side and "right side".

According to another aspect of the invention, the wing portions comprise plane anterior surfaces that are both aligned within one plane. These two anterior surfaces shall be parallel to a transepicondylar axis in an assembled state when viewed in the proximal direction. This design helps the surgeon to easily visualize the anatomical landmarks. Especially the wing portions are positioned within the area of lateral cut-outs of the main block, so that the surgeons when viewing in the proximal direction can see the distal face of the femur and can verify the transepicondylar axis alignment via the anterior surfaces. When aligned, two holes can be drilled through the drilling holes in the proximal direction for referencing.

According to another aspect of the invention, with reference to a virtual line connecting the two referencing orientation points, preferably in the form of the two drilling holes, the indicator wall may be placed on an opposite side as the connecting unit in the anterior posterior direction. In other words, the indicator wall and the connecting unit are at opposite sides of the reversible orientation guide.

Preferably, the anterior stylus may be a separate component and may be adapted to be detachably coupled and uncoupled to the main block. Especially when the anterior stylus can be coupled to main block on a left or right side (that means in the medial-lateral direction) and the anterior stylus can by removably coupled and uncoupled, only one anterior stylus is needed for the system and a number of components and thereby, besides cost savings, a complexity can be reduced.

Preferably, the main block is designed symmetrically to a plane of symmetry (S) wherein the plane of symmetry extends in a proximal-distal direction and the anterior-posterior direction. This makes the design and construction simple and efficient. Further, the main block is adapted to be used for a right joint or knee as well as for a left joint or knee.

According to an aspect of the invention, the main block may have a left receiving opening, preferably with a circular cross-section, having a left longitudinal axis and a right receiving opening, preferably with a circular cross-section, having a right longitudinal axis, wherein preferably the right longitudinal axis is parallel to the left longitudinal axis. Further the anterior stylus may comprise a stylus adapter portion, preferably having an essentially cylindrical outer shape, that form fits in the left receiving opening and the right receiving opening so as to be detachably coupled and uncoupled to the main block. With this configuration the stylus adapter can be placed in the first receiving opening that is preferably in the form of a bore hole, as well as in the right receiving opening, preferably as well in the form of a bore hole. When in the form of a bore hole, the bore holes are in the anterior-posterior direction and parallel to each other. Preferably, the length of each bore hole is the same and preferably at least two times of the dimension as a diameter of the bore holes. Preferably, the diameter of the receiving openings, especially in the form of the bore holes, are the same.

Preferably, the anterior stylus is equipped with a snap-fit system that snap-fits to the receiving opening, especially to the bore hole, when fully inserted. In other words, the anterior stylus has a force enabled form fitting click system that, when fully inserted in a receiving opening, prevents the anterior stylus from being removed or being removed easily. The snap-fit system serves as a retention force for an inserted anterior stylus.

Preferably, the stylus adapter portion has a central through slit/through slot/slit through perpendicular to a longitudinal midline of the adapter portion, so that two elastic legs are formed. Preferably, the stylus adapter portion may further comprise at a free end of each elastic leg a radial outwardly protruding snap-in nose in order to axially snap-fit the anterior stylus in each receiving opening by force locking form fit. The elasticity of the elastic legs and the through slit between the two elastic legs as a space allows the legs to slightly bend radial inwardly. In combination with the snap-in nose that protrudes radially outwards, the adapter portion when inserted, needs a specific force against the elasticity to press the elastic legs together in order to reduce a dimension of a contour of a cross section of the adapter portion. However, when inserted in the receiving opening, especially in the bore hole, and the snap-in nose is not limited any more in the radial direction, the elastic legs can again bend radially outwardly in its non tensioned state. Thereby the snap-in noses forms an undercut in the direction of the right or left longitudinal axis and prevents the anterior stylus from falling out of the receiving opening.

Preferably, the anterior stylus is adapted to be rotatable to the main block within a rotation range that is geometrically limited to have a more precise sizing. Thus, the anterior stylus can be rotated, especially about an axis in the anterior-posterior direction, to place the tip of the anterior stylus to the anterior surface of the femur for the left knee as well as for the right knee. With the limitation of its rotation in at least one direction of rotation, preferably in two directions, a precise size can be measured.

According to another aspect of the invention, the adapter portion has at least one, preferably two indentations at the radial outer surfaces or sides that are at or in the area of the beginning of the through slit. With other words, in the posterior-anterior direction the indentation is preferably at the same position as the beginning of the through slit.

According to another aspect, the main block may comprise two feet and, when viewed at a front (in the proximal direction), between the docking unit and the respective one of the two feet, a fixation block is arranged each having a fixation hole perpendicular to the plane back surface for fixation. These fixations holes allows a surgeon to fix/pin the main block to the distal face of the femur.

Preferably, between the left receiving opening and the right receiving opening, the main block may comprise an upper aperture, that preferably extends from a receiving block of the receiving openings of the left side to a receiving block of the receiving openings of the right side in the lateral-medial direction in order to improve a visualisation of the distal face of the femur. Further, the upper aperture may have a dimension in the posterior-anterior direction that is half of the length of the main block in the in the posterior-anterior direction. Preferably, the size/dimension of the upper aperture in the medial-lateral direction is the size in the anterior-posterior direction. Preferably the upper aperture has a rectangular contour, with especially rounded corners.

Preferably, the anterior stylus comprises a reception/intake and a stylus tab that is slidingly arranged within the reception in order to adjust a position of the stylus tip. More preferably, the reception may further comprise a snap-fit system or spring system that acts on grooves of the posterior side of the stylus tab in order to snap-fit the stylus tab into its current position and to indicate discrete sizes. By doing this, only discrete steps of adjustments can be performed, since the stylus tab snaps in place. Further, a restraining force is implemented by the snap-fit system. Preferably the snap-fit system may be in the form of a spring biased member, that is pretensioned in the anterior direction or in a combination of the anterior and distal direction. The posterior surface of the stylus tab preferably has grooves, preferably grooves that are channel like and extend in the medial-lateral direction, that interacts with the pretensioned member. The reception may be in the form of a C having two snap-in grooves on two opposite sides, like a slider, wherein the stylus tab can be slidingly repositioned.

The object of the invention regarding a generic knee arthroplasty system is solved by comprising a femoral sizer system according to present invention. With such a knee arthroplasty system, an operation can be made more efficient and can be accelerated due to the faster determination of size, its ease of use and its more precise measurement.

Further, the object of the invention regarding a method for using a femoral sizer system according to the present invention is solved by the steps:

Positioning the main block of the femoral sizer system with respect to the femur for distal and posterior referencing;

Selecting a reversible orientation guide with a specific angle of external rotation;

Depending on the operation of a left or right knee joint (femur), rotating the reversible orientation guide so that the orientation guide is suited for the left or the right femur;

Docking the orientation guide with its connecting unit to the docking unit of the main block;

Preferably refining an alignment of the main block to the anatomical landmarks;

Preferably confirming the selection of the right angle of external rotation of the orientation guide;

Fixing of the main block of the femoral sizer system to a processed distal end of the femur with use of the fixation holes;

Adjusting the anterior stylus in its position so that the tip contacts the anterior surface and determining the size with help of the scale;

BRIEF DESCRIPTION OF THE DRAWINGS

The invention is explained in more detail below using the preferred embodiments with the aid of the figures.

The figures are of a schematic nature and intended to improve the understanding of the disclosure of the invention. Same elements are referenced with the same reference signs.

DETAILED DESCRIPTION

FIGS. 1-6 and 8 show a femoral sizer system 1 for knee arthroplasty according to a preferred embodiment of the present invention and components, wherein FIGS. 2-4 and 8 show the sizer system 1 attached to a left femur F.

Figure 1:
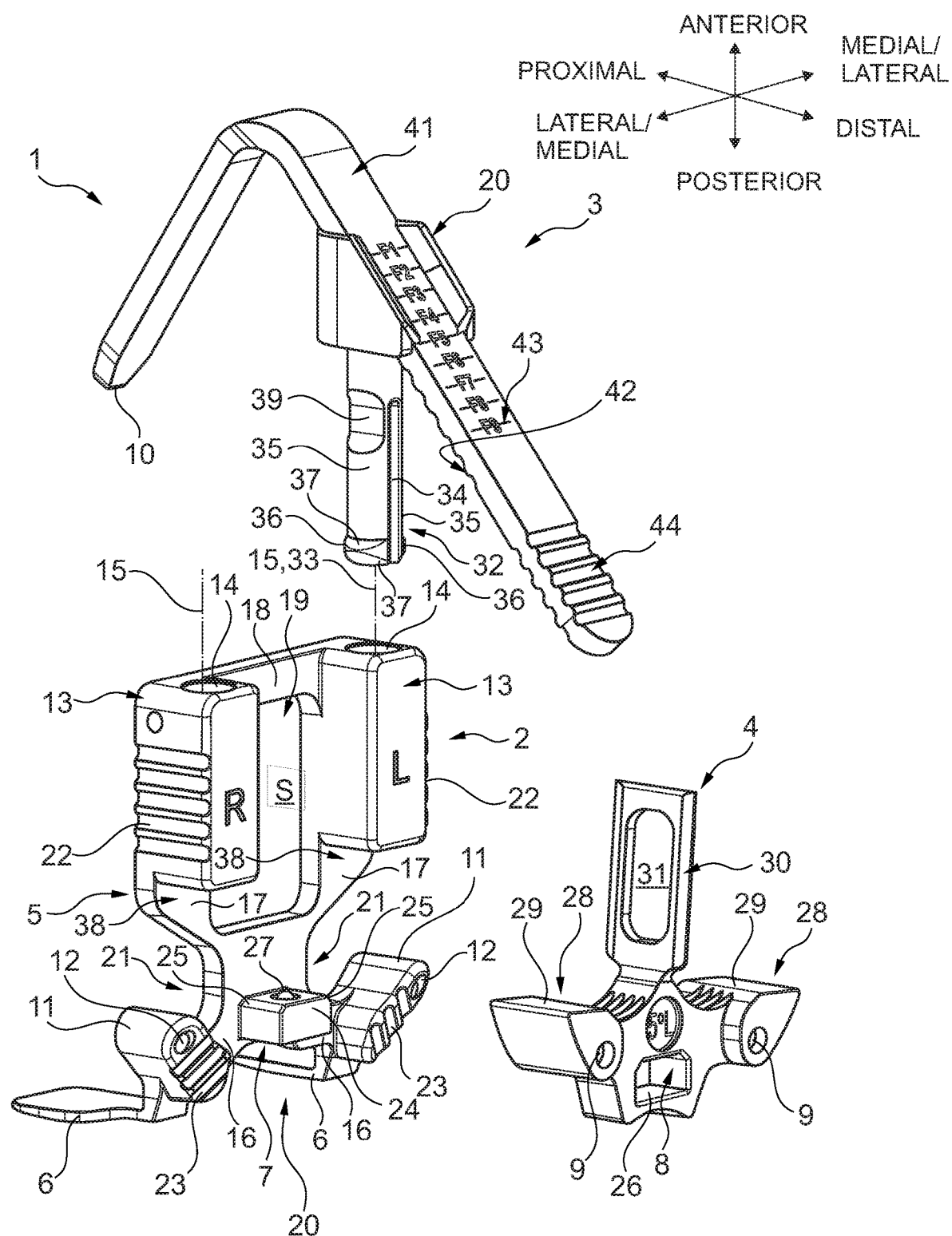
FIG. 1 is a perspective view of a femoral sizer system according to a preferred embodiment of the invention in an exploded view.

As can be seen in FIG. 1, the femoral sizer system 1 (in the following called sizer system) that is in FIG. 1 in an disassembled state, comprises three separate components/modules in the form of a main block 2, an anterior stylus 3 and a reversible orientation guide 4 (in the following called to orientation guide). In this embodiment, the sizer system 1 even comprises a set of two orientation guides 4, 4' with two different degrees of external orientation rotation, namely 3 degrees and 5 degrees. These three modules 2, 3, 4 (, 4') can manually be assembled together in an assembled state and can be disassembled again in an disassembled state without any tools necessary, wherein the main block 2 constitutes the base for a common connection.

Figure 2:
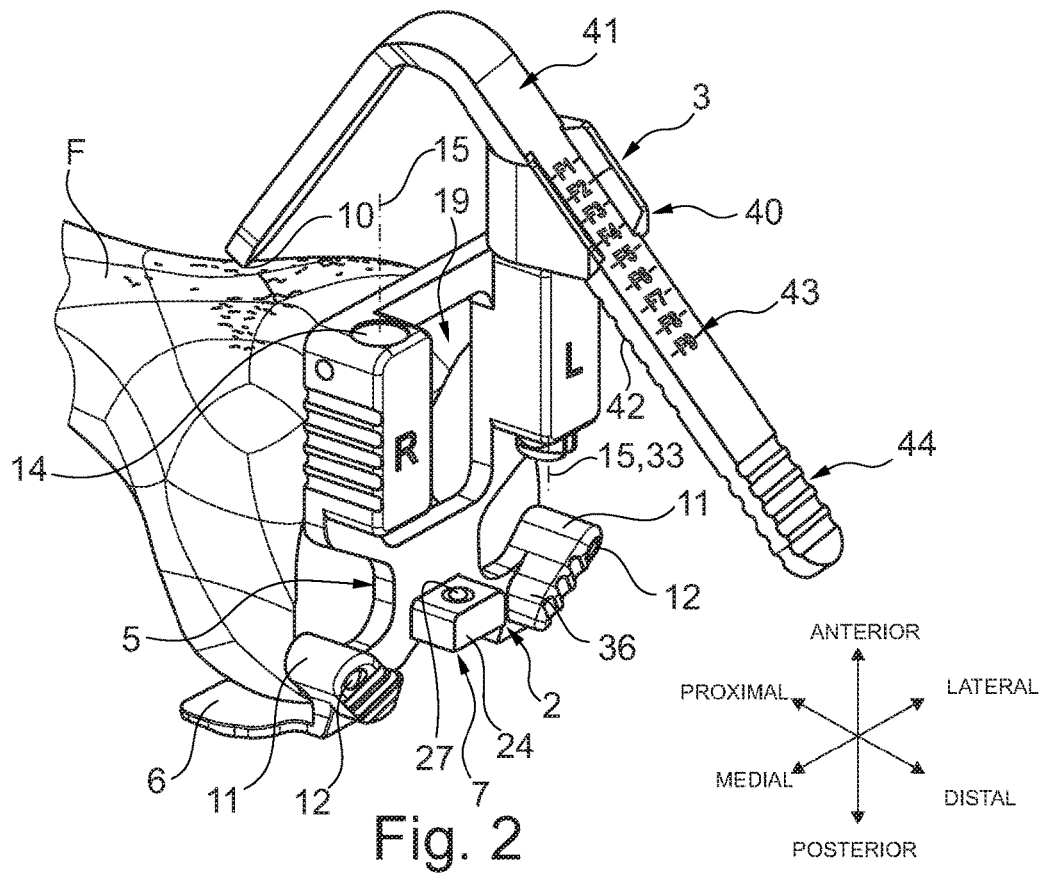
FIG. 2 is a perspective view of the femoral sizer system of FIG. 1 in an assembled state that stands in contact with a distal face of a femur of a patient.

The main block 2 has a plane (femoral) back surface 5 that faces in the proximal direction for being placed in contact with a distal face of a processed/resected femur F, respectively the condyles of a femur F (see FIG. 2). The main block 2 is designed symmetrical to a symmetry plane S. In this embodiment, two fixed feet 6 extend mainly perpendicular to and away from the back surface 5 starting from the back surface 5 in the proximal direction for posterior referencing (posterior face) of the condyles of the femur F.

In contrast to the prior art, the main block 2 itself is not adjustable for implementing an external rotation but constitutes a static block (construct/design) with fixed feet 6. Instead, for external rotation, the sizer system 1 has the following special configuration.

Specifically, the main block 2 comprises a docking unit/docking section 7 in the form of a protruding block in the distal direction that interacts with a corresponding connection unit 8 of the reversible orientation guide/reversible orientation block 4, 4' (see as well FIG. 6) in the form of an through (guide) opening/aperture that extends through the whole orientation guide 4, 4' from a first side to a second side averse the first side. Due to the design of the docking unit 7 and the connection unit 8 in form of a reversible plug-in connection, the (removable) orientation guide 4, 4' can be detachably coupled and uncoupled to the main block 2 in a reversible way so that two different sides of the orientation guide 4, 4' that are avers to each other can each face the main block 2 depending on the plug direction of the orientation guide 4, 4'. In other words the orientation guide 4, 4' can be rotated or the side can be switched/flipped/reversed for a left knee or a right knee by a user and then assembled to the main block 2. The orientation guide 4, 4' thus has two docking directions that are opposite to each other for docking with the main block 2. Specifically, the connecting unit 8 is adapted to have two possible docking directions and depending on the elected docking direction, the first side or the second side of the orientation guide 4, 4' faces the main block 2.

The orientation guide 4, 4' has, in an assembled state of the sizer system 1, two referencing orientation points I the form of two drilling holes 9 for referencing a drilling of an external drilling tool and for insert of fixation/referencing pins. As explained in the following, a transversal line that connects the two drilling holes 9 with each other is rotated by +5° or −5° and for the second orientation guide by +3° or −3° with reference to the connecting unit 8 and thereby to the main block 2. Thus, when the reversible orientation guide 4, 4' is attached to the main block 2, depending on the side of the orientation guide 4 that faces the main block 2, the transversal line that connects the two holes 9 are rotated by 5°, respective 3° for the second orientation guide 4', in a positive rotation direction or a negative rotation direction with reference to the main block 2 and its symmetry plane S.

Figure 8:
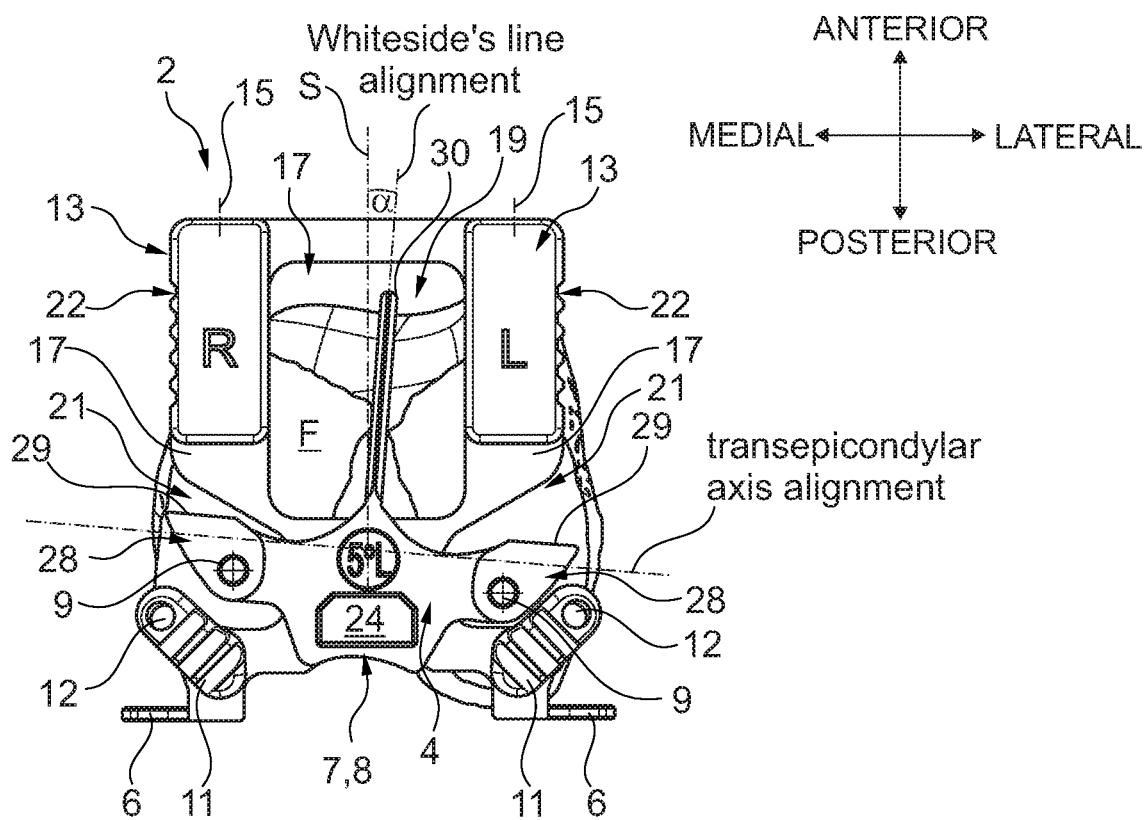
FIG. 8 is a front view of the femoral sizer system of the preferred embodiment that is attached to the distal face of the femur.

In conclusion, different to the prior art, the femoral sizer system 1 of the present invention does not need different sets of orientation guides for the left knee and for the right knee, but instead with only one reversible orientation guide 4, 4', an angle of external orientation rotation a can be determined for the left knee (joint) as well as for the right knee (joint). For example, for the left knee a first alignment/orientation of the orientation guide 4, as shown in FIG. 8, indicated with a visible "5° L" to a medical expert, can be used and if the medical expert wants to switch to the right knee, he just flips the orientation guide 4 around its central axis by 180° (perpendicular to an axis of the guide opening 8) so that a flipped alignment is used. By doing so, the angle of external rotation thereby switched its sign from +5° to −5°. The same applies to the second orientation guide 4' with +3° and −3°.

In addition, due to the small docking unit 7 and the small connecting unit 8, for a surgeon, a field of vision can be expanded and improved as well.

The sizer system 1 comprises the anterior (surface) stylus 3 that has a stylus tip/point 10 for being placed in contact with an anterior face of the femur F (see FIG. 2). The anterior stylus 3 (called stylus in the following) is a removable component/module that is attachable and detachable to the main block 2. Further, the stylus 3 is adapted to adjust a position of the stylus tip 10. When the sizer system 1 is placed in contact with the posterior condyles of the femur, the anterior stylus tip 10 of the anterior stylus (tab) 3 is adjusted to be in contact with the anterior surface of the femur F in order to determinate its size.

In consequence, the present femoral sizer system 1 allows in a few steps to evaluate a size of the femur F (depending on the size of the implant) and an external rotation a is determined and aligned easily according to the anatomic landmarks. The sizer system 1 is a simple system that can be used easily without a lot of adjustments and that is also less invasive, since it is less voluminous with more apertures.

The sizer system 1 is described in more detail in the following. The main block 2, that is symmetric to the Symmetry plane S, has, when viewed in the proximal-distal direction, an X-shape, wherein in the center of the X, the docking unit 7 is provided and on lower legs 16 of the X, on each leg 16, a fixation block 11 is provided having an fixation hole 12 in the distal-proximal direction. These fixation holes 12 serve for fixation of the main block 2 to the femur. The fixation block 11, that has an oval shape when viewed in the proximal direction and is aligned V-shaped to each other (approximately 90° rotation to each other about an intersection of a virtual extension of a longitudinal line of the fixation blocks 11) is followed by a foot of the two feet 6 to its free end, wherein the feet 6 each extend in the proximal direction. Upper legs 17 of the X each comprise a receiving block 13 each having a receiving opening 14 with a longitudinal axis 15. The two receiving blocks 13 are in the design of a rectangular block extending in the anterior-posterior direction. Therein, both longitudinal axis 15 of the receiving openings are parallel to the back surface 5 and parallel to each other. The longitudinal axis are both aligned in the anterior-posterior direction. These receiving openings 14 are adapted to receive the stylus 3, as explained later on. On the outer side of the receiving blocks 13, facing away from the sizer system 1, in each outer side a hole in the medial-lateral direction is provided that implements an opening to the receiving openings 14 for fixation of the anterior stylus 3.

Between the two upper legs 17 of the X respectively between the two receiving blocks 13 of the main block 2, at an anterior side, a connection bridge (strut) 16 for a stabilization is implemented connecting the two receiving blocks 13 with each other.

In other words, the main block 2 has kind of a plane metal sheet with a plane back surface 5, that has, when viewed in the proximal-distal direction around a central portion with the docking unit 7, four cut outs (apertures) 19, 20, 21, two cut-outs 21 in the lateral-medial direction (on each side of the central portion) and two cut outs 19, 20 in the posterior anterior direction (on each side of the central portion), wherein the upper cut out 19 is in the form of an aperture due to the connection bridge 18. Starting from this plane metal sheet, all blocks, the receiving blocks 13, the fixation blocks 11 and the docking unit 7, extend in the distal direction. The two feet 6 extend in the opposite direction, namely in the proximal direction, having a flat surface that contacts the posterior side of the femur (see FIG. 2 i.e.).

The receiving blocks 13 both have on its outer side in the lateral-medial direction a grooved surface 22 for enhanced handling of a medical expert. Likewise, the fixation blocks 11 have a grooved surface 23 on its outer side in the distal direction as well.

The docking unit 7 is in the specific form of a rectangular block 24 that extends in the proximal direction that has two chamfered edged 25 of its four edges on its upper part (upper (direction) means in the anterior direction, lower (direction) means the posterior direction). Likewise, the guide opening 26 of the orientation guide 4, 4' is in the form of a rectangular aperture with two chamfered edges on its upper part (when seen in the assembled state). Thus, since the chamfered edges are symmetric to the symmetry plane S, the orientation guide 4, 4' can be rotated about an axis in (roughly speaking) the anterior-posterior direction and still can be docked to the main block 2, respectively the docking unit 7 of the main block 2. Any other docking such as upside-down is excluded because of the specific geometry with the chamfered edges. The length of the rectangular block 24 in the distal direction is the same length as the guide opening 26.

The rectangular block 24 of the docking unit 7 has on its anterior side a submerged spring biased ball 27 that is positioned in the centre of a surface of the anterior side for force locking form fitting with an upper side of the guide opening 26. In specific, an upper surface (anterior surface) of the guide opening 26 has in its centre a complementary trough or recess that interacts with the locking ball 27 and implements a click-system for partly securing the orientation guide 4, 4' and for giving a feedback to the surgeon, whether the orientation block 4, 4' is attached/coupled/assembled correctly to the main block 2. The locking ball 27 is pushed in the anterior direction in a spring biased manner. Since only a small part of the locking ball extends through the surface of the rectangular block 24, the upper surface of the guide opening 26 can push the locking ball 27 against its spring biased force in the posterior direction and when the orientation guide 4, 4' is in the right place, the locking ball 27 springs back and stands/sticks into the trough/recess.

The two feet 6 are each in the form of plate shaped portions with a plane anterior surface that are brought in contact with the posterior condyles of the femur for posterior referencing. The plane anterior surface of the feet 6 together with the back surface 5 of the main block 2 are in an L-shape with 90° between the two surfaces.

Figures 5, 6:
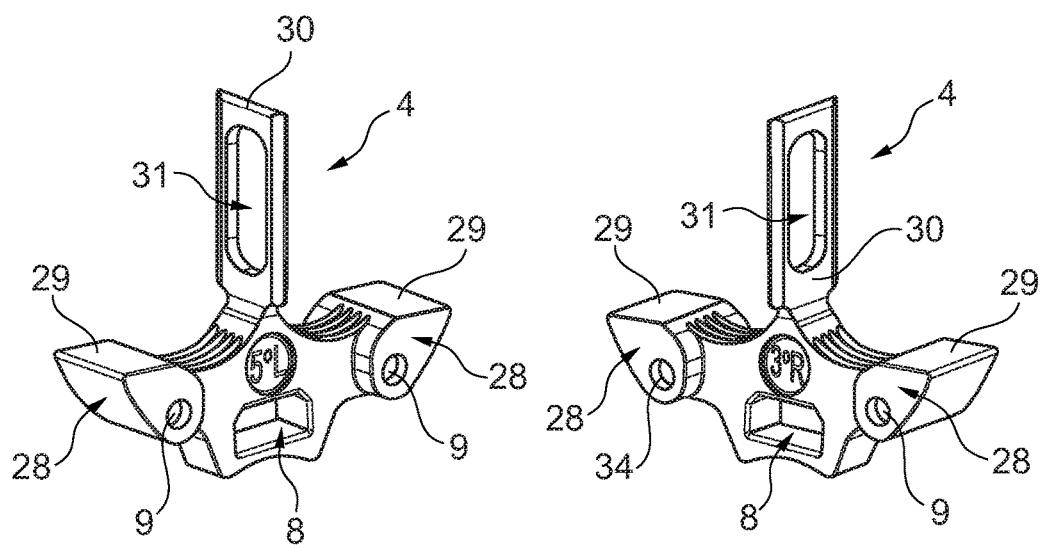
FIG. 5 is a perspective view of a first reversible orientation guide with a predefined angle of 5° of the femoral sizer system of FIGS. 1-4.
FIG. 6 is a perspective view of a second reversible orientation guide with a predefined angle of 3° of the femoral sizer system of FIGS. 1-4.

As can be seen especially in FIGS. 5 and 6, the orientation guides 4 and 4' have two wing shaped portions 28 extending on each side in the medial-lateral direction. When viewed in the proximal direction (or a top view/front view) the form is like a raindrop having a pointed end at the outer directions (pointing away from each other). These wing shaped portions 28 fit in both reversible orientations in between the receiving blocks 13 and the fixations blocks 11 having a distance to one another. An anterior surface/side 29 (in an assembled state) of the wing shaped portions 28 is plane and both surfaces of both wing shaped portions 28 are in one plane that is (in an assembled state) rotated 5 degrees or 3 degrees respectively about an axis in the proximal-distal direction that lies within the symmetry plane S, so that the anterior surface 29 is not parallel with the medial lateral-direction and not perpendicular to the symmetry plane S but rotated by 3 or 5 degrees. Moreover, the drilling holes 9 that are provided in the wing shaped portions 28 are as well rotated by degrees or 3 degrees respectively about an axis in the proximal-distal direction. In other words, a transversal connecting line between the two drilling holes 9 are parallel to the anterior surfaces 29 and both are rotated about an axis of rotation in the proximal-distal direction that lies within the symmetry plane S by an angle of external rotation a.

In other words, the orientation guide 4, 4' is, when viewed from the front, designed symmetrical to a (guide) symmetry plane but the guide opening 26 is rotated by an angle of rotation a to the (guide) symmetry plane so that when assembled, the whole orientation guide 4, 4' is rotated by the angle of rotation a, since the guide opening 26 is the connecting structure and thus defines the alignment.

The orientation guide 4, 4' further comprises an indication wall 30 that extends perpendicular to a virtual connection line between the two drilling holes 9. In addition the wall extends in the proximal-lateral direction, but with a smaller dimension. This indicator wall 30 is used for determining and verifying a correct alignment to the Whiteside's line. Further the wall indicator has a wall aperture 31 that faces the lateral-medial direction. This wall aperture improves the weight of the orientation block as well as a view for a surgeon.

In FIGS. 1-4, the anterior stylus 3 is shown. The anterior stylus 3 has a stylus adapter portion/section 32 in a cylindrical form (cylinder) with a circular cross section (circular outer contour) having a longitudinal midline 33 that is adapted to fit into both, the left and right receiving openings 14 of the main block 2. Thereby, the anterior stylus can be attached to and detached from the main block 2. Due to its geometry, the adapter portion 32 and with it the stylus 3 can be rotated about the longitudinal axis 15 of each receiving opening 14.

Further, the adapter portion 32 comprises (see FIG. 1) a central slit through/through slit 34 perpendicular to the midline 33, so that two elastic legs 35 are formed. Further, the adapter portion 33 comprises at a free end of each leg 35 a radial outwardly protruding snap-in nose 36 in order to implement a snap-fit system and to axially secure the anterior stylus 3 in each receiving opening 14 by force locking form fit. The two elastic legs 35 can be pressed together against the elastic force and the adapter portion 32 can be inserted into the receiving opening 14 in the left side (L) or on the right side (R) of the receiving blocks 13. The snap-in nose 36 has in an anterior-posterior-direction on both sides ramp structures 37 to simplify/facilitate an introduction/insertion as well as an extraction of the adapter portion 32. When inserting, the stylus 3 can simply be pushed in the posterior direction and the ramp structure 37 on the posterior side of the snap-in nose 36 pushes, due to its geometry, the elastic legs 35 together until the adapter portion fits in the receiving opening 14. Then the stylus 3 is pushed until the end (the stylus 3 abuts the main block 2) where the snap-in noses 36 is geometrically released in the radial direction against its pretensioning, since the length of the adapter portion 32 is a bit longer than the length of the receiving openings 14.

Another advantage of the specific geometry of the snap-in noses 36 together with an abutting portion 38 beneath the receiving blocks 13 of the main block 2, is that a rotation is limited in both rotation directions. The snap-in noses 36 normally extend in the lateral-medial direction but when the stylus is rotated about its longitudinal midline 33, the snap-in noses 36 rotate as well. Since the design of the main block 2 is that the receiving openings 14 are very close to a distal surface, here the abutting portion 38, the protruding snap-in noses 36 will abut the abutting portion 38 within a certain degree of rotation. In conclusion, the stylus is axially (removably) fixed by the snap-in noses 36 but has a certain degree of freedom of rotation about its longitudinal midline 33. The anterior stylus 3 is able to rotate in order to reach a better referencing point of the anterior surface (cortex). This rotation is limited to have a more precise sizing.

Figure 3:
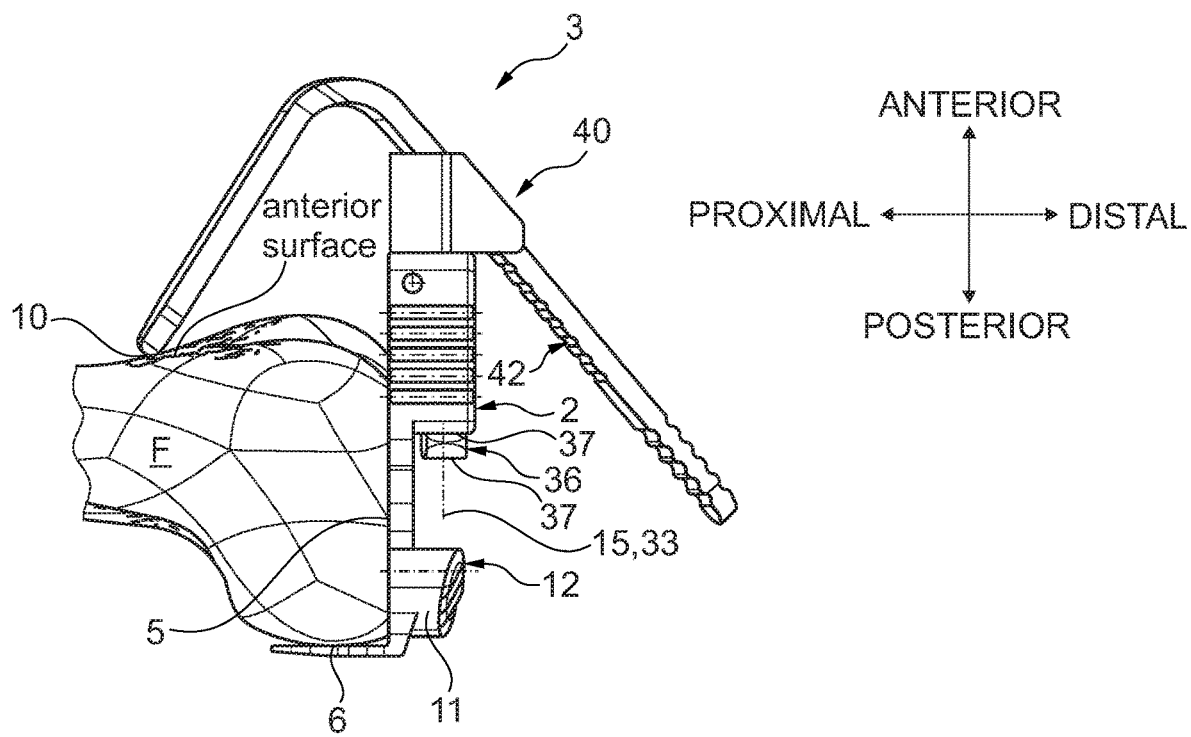
FIG. 3 is a side view of the femoral sizer system of FIGS. 1 and 2 viewed in a medial-lateral-direction.
Figure 4:
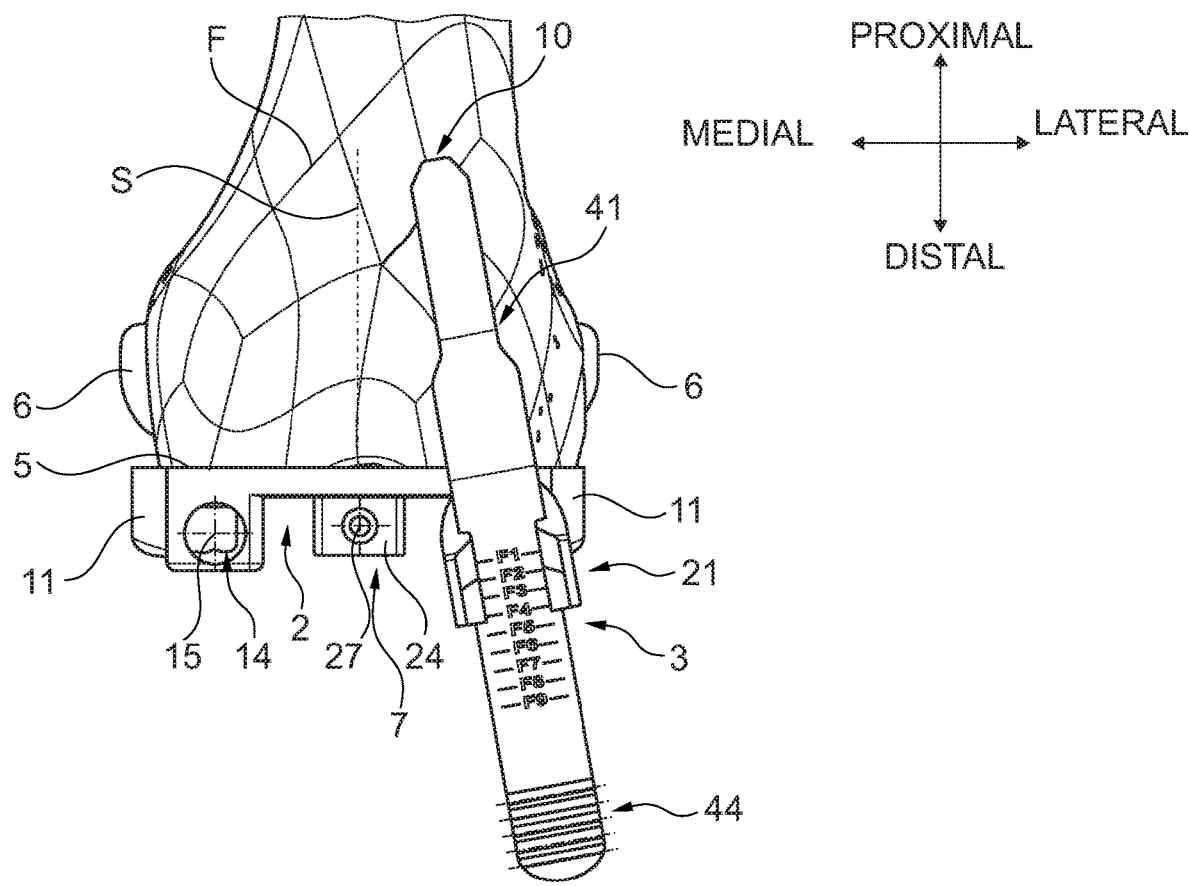
FIG. 4 is a top view of the femoral sizer system of FIGS. 1-3 viewed in a posterior-anterior-direction that is attached to the femur.

The stylus 3 further has an indentation/recess 39 at the radial outer sides at/in the range of a beginning of the through slit 34. This indentation 39 helps to improve the elasticity of the elastic legs 35. As can be seen in FIG. 1, 2 or 3 and as described before, a bore hole in the lateral-medial direction is placed in the receiving block 13. For the right receiving block, the bore hole is placed in its outer side in the lateral direction, for the left receiving block in the medial direction. With this bore hole and the indentation 39, it is possible to fixate the adapter portion 32 of the anterior stylus 3 in place.

The adapter portion 32 of the stylus 3 is followed by a reception 40 that is adapted to slidingly accommodate a stylus tab 41 having the stylus tip 10. In this embodiment, the stylus tab is in form of a bent metal sheet that is, viewed in the medial-lateral direction, L-shaped. As can be seen in FIG. 3 for example, the reception 40 (or its sliding surface) is not parallel to a proximal-distal direction, but has an inclination of about 45° to it, so that when the stylus tab 41 is sliding inside the reception 40, the stylus tab 41 (when the stylus 3 is not rotated) is moved in a proximal-distal direction as well as in an anterior posterior direction. Likewise the stylus tip 10 moves in these directions as well. On top of the stylus tab 41 within the range of the reception 40 a scale 43 for indicating the size is provided. Depending on the relative sliding in the reception 40 and the contact to the anterior surface of the femur F, a surgeon can determine the size by reading the scale 43.

In addition the stylus tab 41 has stylus grooves 42 on its posterior surface (facing the sliding surface of the reception 40) and the reception 40 has a spring biased member (spring system, not shown) that abuts the stylus grooves, so that a click-system or snap-fit system is implemented and only discrete steps of sliding the stylus tabs 41 can be performed. Further the stylus tab 41 is locked in place. The anterior stylus 3 can be slightly locked for each size thank to click-system/spring system with the spring biased member.

At its distal end, the stylus tab 41 has finger grooves 44 in order to facilitate a handling of the stylus 3.

Figure 7:
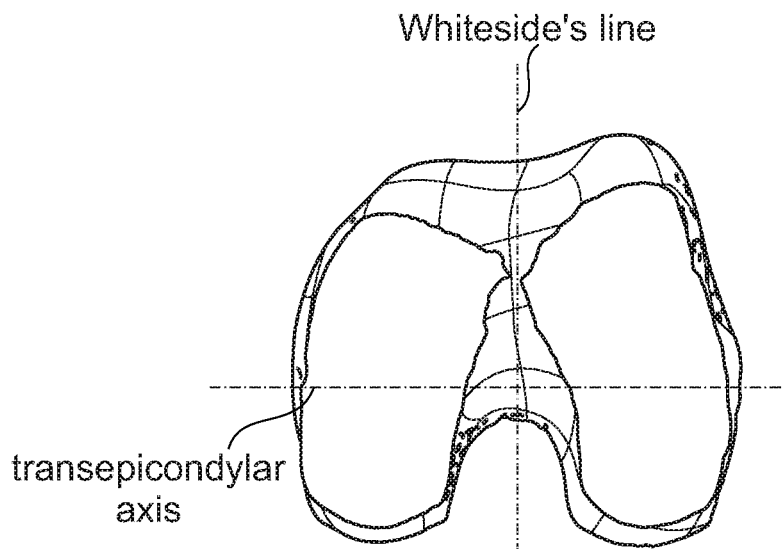
FIG. 7 is for the understanding a front view of the distal end face of the femur with the anatomic landmarks in form of the (trans)epicondylar axis and the Whiteside's line.

In FIG. 7, a distal face of the femur F is shown for illustration with its anatomical landmarks of a transepicondylar axis and a Whiteside's line. These landmarks are the references for the sizer system 1.

In FIG. 8 the main block 2 of the sizer system 1 is positioned at the distal front of the femur F. Due to the large upper aperture 19, a surgeon or medical expert has a good view onto the femur F and an enhanced visualisation and visibility in order to determine the Whiteside's line alignment. Likewise, due to the lateral cut outs 21, a good visualisation for the transepicondylar axis alignment can be achieved. The orientation block 4 is docked to the docking unit 7 (here for the left knee, indicated with the letter "L") and the indicator wall 30 that is in front of the upper aperture 19 indicates the correct alignment in front of the femur F. Here the angle of rotation a is +5° with reference to the symmetry plane S. Since the indicator wall 30 stands perpendicular to the connecting line between the drilling holes 9, the drilling holes 9 for referencing are as well rotated by +5°.

A surgeon can thereby easily adjust the external rotation a by selecting the correct orientation guide 4 or 4' and compare the indication wall 30 and the anterior surface 29 with the respective anatomical landmarks.

The invention claimed is:

1. A femoral sizer system for knee arthroplasty, the femoral sizer system comprising:
   a main block having a plane back surface for being placed in contact with a processed distal face of a femur for distal referencing, at least one fixed foot extending mainly perpendicular to and away from the back surface for posterior referencing, and a docking unit for docking with a connecting unit;
   an anterior stylus having a stylus tip for being placed in contact with an anterior face of the femur, the anterior stylus being attached or attachable to the main block and being adapted to adjust a position of the stylus tip; and
   a reversible orientation guide having at least two referencing orientation points that are provided and adapted for implementing referencing pins in the femur for referencing anatomical landmarks, and having the connecting unit corresponding to and interacting with the docking unit, the reversible orientation guide being adapted to be reversibly, detachably coupled to and uncoupled from the docking unit of the main block via its connecting unit with at least two different sides of the reversible orientation guide resulting in two different positions of the at least two referencing orientation points relative to the main block, so that the femoral sizer system is configured to be used for the right knee joint as well as for the left knee joint.

2. The femoral sizer system according to claim 1, wherein the docking unit and the connecting unit are adapted to be form fitting together via its respective geometry for a first side of the reversible orientation guide facing the main block as well as for a second side of the reversible orientation guide facing the main block.

3. The femoral sizer system according to claim 2, wherein the docking unit of the main block comprises of a block protruding perpendicular to the plane back surface in a direction opposite to the extension of the at least one foot, and the connecting unit of the reversible orientation guide is a guide opening complementary to the block to implement a lock and key principle.

4. The femoral sizer system according to claim 1, wherein the docking unit of the main block comprises a locking member that interacts with the connecting unit, in order to implement a snap-fit system to keep the reversible orientation guide in place and to give a feedback to a user that the reversible orientation guide is connected properly.

5. The femoral sizer system according to claim 4, wherein the locking member is in the form of a locking ball and is pretensioned in the anterior direction and interacts with the connecting unit via a corresponding trough or recess of the connecting unit.

6. The femoral sizer system according to claim 1, wherein the reversible orientation guide is designed axial symmetrically except for the connecting unit that is rotated by an angle of rotation about an axis that is parallel to the respective symmetry plane in order to implement an external rotation.

7. The femoral sizer system according to claim 6, wherein the reversible orientation guide is, when viewed at a front side, in a T-shape, having two wing portions, each wing portion comprising one of the at least two referencing orientation points for transepicondular axis alignment, and having an indicator wall that extends perpendicular to a virtual line connecting the at least two referencing orientation points for referencing the Whiteside's line.

8. The femoral sizer system according to claim 7, wherein with reference to the virtual line connecting the at least two referencing orientation points, the indicator wall is on an opposite side to the connecting unit.

9. The femoral sizer system according to claim 1, wherein the anterior stylus is a separate component and is adapted to be detachably coupled and uncoupled to the main block.

10. The femoral sizer system according to claim 1, wherein the main block is designed symmetrically to a plane of symmetry.

11. The femoral sizer system according to claim 1, wherein
the main block has a left receiving opening having a left longitudinal axis and a right receiving opening having a right longitudinal axis, and
the anterior stylus having a stylus adapter portion that form fits in the left receiving opening and in the right receiving opening so as to be detachably coupled and uncoupled to the main block.

12. The femoral sizer system according to claim 11, wherein the stylus adapter portion has a central through slit perpendicular to a longitudinal midline of the stylus adapter portion, so that two symmetric elastic legs are formed, the stylus adapter portion further comprising at a free end of each elastic leg a radial outwardly protruding snap-in nose in order to axially snap-fit the anterior stylus in each receiving opening by force locking form fit.

13. The femoral sizer system according to claim 11, wherein the main block comprises an upper aperture between the left receiving opening and the right receiving opening in order to improve a visualization of the processed distal face of the femur.

14. The femoral sizer system according to claim 11, wherein the left longitudinal axis is parallel to the right longitudinal axis.

15. The femoral sizer system according to claim 11, wherein the left receiving opening and the right receiving opening each having a circular cross-section, and the stylus adapter portion having a corresponding cylindrical outer surface.

16. The femoral sizer system according to claim 1, wherein the anterior stylus is adapted to be rotatable to the main block within a rotation range that is limited in order to have a more precise sizing.

17. The femoral sizer system according to claim 1, wherein the anterior stylus comprises a reception and a stylus tab with the stylus tip, wherein the stylus tab is slidingly arranged within the reception in order to adjust a position of the stylus tab and the stylus tip, the reception further comprising a snap-fit system that acts on grooves of the stylus tab in order to snap-fit the stylus tab into its current position and to allow only discrete steps and sizes.

18. A knee arthroplasty system comprising a femoral sizer system according to claim 1.

19. The femoral sizer system according to claim 1, wherein the at least two referencing orientation points are two drilling holes.

* * * * *